United States Patent [19]

Frohman

[11] 4,146,614
[45] Mar. 27, 1979

[54] THREONYL-VALYLINE LEUCINE CONTAINING PEPTIDES AND PHARMACEUTICAL COMPOSITIONS

[75] Inventor: Charles E. Frohman, Grosse Pointe Woods, Mich.

[73] Assignee: State of Michigan, Lansing, Mich.

[21] Appl. No.: 772,851

[22] Filed: Feb. 28, 1977

Related U.S. Application Data

[63] Continuation-in-part of Ser. No. 669,526, Mar. 23, 1976, abandoned.

[51] Int. Cl.$^2$ .................... A61K 37/00; C07C 103/52
[52] U.S. Cl. .............................. 424/177; 260/112.5 R
[58] Field of Search .................. 424/177; 260/112.5 R

[56] References Cited

U.S. PATENT DOCUMENTS

| | | | |
|---|---|---|---|
| 3,873,722 | 3/1975 | Smythies | 424/177 |
| 3,885,034 | 5/1975 | Risse et al. | 424/177 |
| 3,932,623 | 1/1976 | Wilson | 424/177 |

OTHER PUBLICATIONS

Kolb, Modern Clinical Psychiatry, pp. 311-312 (1973).
Harlow, Academy of Medicine (1960), pp. 1-41.
Beckett et al., The American Journal of Psychiatry 119, pp. 835-842 (1963).
Heath, Diseases of the Nervous System 33, pp. 157-163 (1972).
Bergen et al., Serological Fractions in Schizophrenia, p. 67 (1963).
Carey, Biological Psychiatry 8, pp. 75-88 (1974).
Caldwell et al., Biological Psychiatry 8, pp. 235-244 (1974).
Frohman et al., Molecular Basis of Some Aspects of Mental Activity 2, pp. 241-255 (1967).
Frohman, Mind as a Tissue, pp. 181-195.
Frohman et al., Recent Advances in Biological Psychiatry 7, pp. 45-51 (1964).
Frohman et al., Biological Psychiatry 7, pp. 53-61 (1973).
Harmison et al., Biochemistry 21, pp. 4485-4493.
Chemistry and Biology of Peptides, pp. 423, 427, 428, (1972).

*Primary Examiner*—Delbert R. Phillips
*Attorney, Agent, or Firm*—Bernard & Brown

[57] ABSTRACT

Polypeptides, omega-N-acylated and/or hydrocarbon-containing esters or amides of polypeptides are useful in the treatment of schizophrenia. The polypeptide-containing materials have a characteristic T-V-L structure, i.e.,

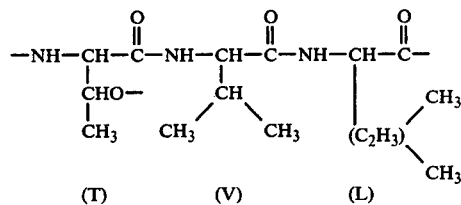

The preferred compositions are N-acylated T-V-L containing polypeptides, especially amides.

37 Claims, No Drawings

THREONYL-VALYLINE LEUCINE CONTAINING PEPTIDES AND PHARMACEUTICAL COMPOSITIONS

This invention is a continuation-in-part of application Ser. No. 669,526, filed Mar. 23, 1976, now abandoned.

This invention relates to compositions of matter that are useful in the treatment of schizophrenia. More particularly, the invention concerns the treatment of schizophrenia by the use of polypeptides, omega-N-acylated and/or hydrocarbon-containing esters of polypeptides. The polypeptides have from three to about eight alpha-aminoacid moieties and a characteristic

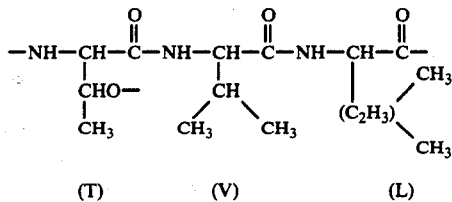

structure, especially such N-acylated T-V-L-containing polypeptides, and the corresponding amides such as, for instance, the N-acyl-threonylvalylleucinamides.

Schizophrenia is the most serious of all the mental illnesses with which the psychiatrist must deal. The incidence rate is approximately one in a thousand, and the prevalence rate approximately one in a hundred. It is responsible for from 25 to 50 percent of all the admissions to state hospitals for the mentally ill and psychiatric services in general hospitals (Kolb, *Modern Clinical Psychiatry*, pp. 311-312, 1973).

The majority of patients who develop this illness have an onset that is slow and insidious, although a small percentage of patients may have an acute onset. The illness is characterized by a disturbance in emotional responses with dulling or inappropriate expressions; by a disturbance in thinking characterized by inability to reach a goal idea, by fragmentation, by a disturbance in associations, blocking, neologisms, etc.; by a withdrawal from the environment and a preoccupation with internalized thoughts; by a loss of the ability to experience pleasure; and most frequently by disturbances in perception as manifested grossly in hallucinations and delusions.

Unfortunately, schizophrenia most frequently begins in late adolescence or early adulthood and, in spite of the use of anti-psychotic drugs, persists by incapacitating the individual more or less for the duration of the individual's life.

There is considerable evidence now that this illness is a genetically determined condition although, undoubtedly, environmental factors, particularly early life experiences, most probably are important too. There seems to be no doubt that there is a basic metabolic disturbance which will be described in detail herein.

Unfortunately, it cannot be absolutely proven that there is an animal model for schizophrenic studies since one can not converse with the animal to establish that it is a schizophrenic. The maternally and sensory deprived Macaque monkeys at the Wisconsin Primate Laboratory are disturbed in behavior (being fearful, aggressive towards themselves, and unable to function sexually), thereby, coming closest in behavior to patients with schizophrenia (Harlow, "The Development of Patterns of Affection", Thomas William Salmon Lectures, New York Academy of Medicine, New York, Dec., 1960). The most severely deprived monkeys have been studied and show a disturbance in an alpha-2-globulin, herein described, of their blood similar to the disturbance that characterizes patients (Beckett, Frohman et al., "Schizophrenic-like Mechanisms in Monkeys", *The American Journal of Psychiatry*, 119:835-842, 1963). Moreover, these monkeys also demonstrated electro-encephalographic disturbances, particularly of the septum of the brain, similar to what have been previously described as characteristic of patients with schizophrenia (Heath, "Electroencephalographic Studies in Isolation-raised Monkeys with Behavioral Inpairment", *Diseases of the Nervous System*, 33:157-163, 1972).

The use of animals, therefore, has been primarily to demonstrate the presence of abnormal metabolic substances in the blood of patients with schizophrenia. When an abnormal blood protein is given to rats in a food reward, rope climbing situation, the rats are slowed down considerably in their performance (Bergen et al., "Further Experiments with Plasma Proteins from Schizophrenics". In: *Serological Fractions in Schizophrenia*, edited by R. E. Heath, p. 67, Paul B. Hoeber, Inc., Medical Book Department of Harper & Row, New York, 1963).

There is some evidence that extracts of the limbic system of the brain of patients who have died, when injected into normal volunteers produces a simulated schizophrenic reaction (Garey, "Focal Electroencephalographic Changes Induced by Anti-septal Antibodies", *Biological Psychiatry*, 8:75-88, 1974). The most consistent studies involve the injection of the isolated alpha-2-globulin from the blood of schizophrenic patients in microliter amounts, into ventricles of rats who have implanted electrodes in the median forebrain bundle. Rats so implanted will reward themselves by pressing a bar as often as they can at the expense of all other activity. When microscopic amounts of the isolated alpha-2-globulin are injected into the ventricles, there is a reduction in the bar-pressing which does not occur when the comparable substance from a control subject is injected. Some of the rats injected with the schizophrenic isolated blood protein may hover over the bar poised as if to press the bar, weaving and unable to continue, simulating a schizophrenic disturbed motor state. The interpretation of the reduction in bar-pressing is that the animal has lost its ability to experience pleasure much as that which characterizes schizophrenic patients (Caldwell, et al., "The Effects of the S-protein on Intracranial Self-Stimulation in the Rat", *Biological Psychiatry*, 8:235-244, 1974).

I have been intimately involved for many years in considerable research efforts devoted to determining the cause of schizophrenia in terms of biochemistry, and to determine psychopharmalogical modes for its treatment. In this work it was found that a high molecular weight protein, estimated as having a molecular weight about 263,000 and being about 80 percent lipid, is more active in schizophrenics than normal individuals, and the more rapidly a schizophrenic deteriorates, the more active is the protein. This protein has been classified as an alpha-2-globulin, and has been referred to as the S-protein; Frohman, C. E.; Latham, L. K.; Beckett, P. G. S.; and Gottlieb, J. S.; "Biochemical Studies of a Serum Factor In Schizophrenia", *Molecular Basis of Some Aspects of Mental Activity*, Vol. 2, Walaas, O., Ed., pp. 241-255, Academic Press, New York (1967); and Frohman, C. E., "Studies on the Plasma Factors in Schizophrenia", *Mind as a Tissue,* Rupp, C., Ed., pp. 181–195, Hoeber Med. Div., Harper & Row, New York. The S-protein when administered to, for instance, rats, blocks the enjoyment of pleasure stimulations in the rats, but does not apparently alter their avoidance response.

Endeavors to reduce the activity of the S-protein in schizophrenics have included obtaining extracts from brains, for example, cattle brain, beef pineal glands, etc., in the search for materials which control the level or activity of the S-protein. Frohman, et al., in "Control of the Plasma Factor in Schizophrenia", *Recent Advances in Biological Psychiatry,* Volume 7, pp. 45 to 51, 1964, described that an isolated protein from animal tissue counteracted the activity of the S-protein. This protein has been named the anti-S-protein and is found in both human and animal tissue. In schizophrenics, S-protein in an alpha-helical conformation is found, whereas, in normal persons the S-protein predominates as a random chain or beta-helical conformation. Production of therapeutic quantities of the anti-S-protein involves great difficulties and high expense, and its extraction for general medical use is impractical. Moreover, the production of a few milligrams of the anti-S-protein from cattle would require the sacrifice of, say, 100,000 cattle. Thus, the natural supply of anti-S-protein is clearly insufficient for treatment of other than a few individuals and would entail an unbearable expense. Other publications relating to these prior studies include the following and the citations therein: Frohman, C. E.; Arthur, R. E.; Yoon, H. S. and Gottlieb, J. S.; "Distribution and Mechanism of Action of the Anti-S-Protein in Human Brain", *Biological Psychiatry,* Vol. 7, No. 1, pp. 53 to 61, 1973; and Harmison, C. R. and Frohman, C. E., "Conformational Variation in a Human Plasma Lipoprotein", *Biochemistry,* Vol. 11, No. 26, pp. 4485–4493, 1972.

It has also been noted in studies in which I have been involved that the extracted anti-S-protein is an antigen. While schizophrenia may be dramatically abated upon the initial administration of the anti-S-protein to a patient, the anti-S-protein is rapidly inactivated through production of antibodies, and subsequently administered anti-S-protein can be so rapidly inactivated that it provides no discernible effect in treating schizophrenia. I have been involved in attempts to break down the anti-S-protein into fragments which may have an acceptable activity in treating schizophrenia without exhibiting the undesirable antigen activity.

In accordance with the present invention, the digestion of the anti-S-protein with, for example, pepsin and trypsin, to provide small peptides of less than about 1000 molecular weight, yields a tripeptide-containing fraction which has been found to be active in reducing the undesired activity of the S-protein. The tripeptide exhibits activity for causing the conversion of alpha-helical S-protein to its random chain conformation. This tripeptide has been characterized as threonyl-valyl-leucine. Work has been undertaken to synthesize this tripeptide, and a substantially pure, i.e., crystalline form, of the tripeptide has been obtained. This tripeptide exhibits activity against the S-protein of schizophrenics, i.e., the alpha-helical conformation of the S-protein is converted to the random form. When administered in tests to counteract the effect of the S-protein in rats the period of effectiveness of the tripeptide is, however, of short duration, therefore frequent periodic doses of the tripeptide would be required in any effective treatment of schizophrenia.

By the present invention, it has also been found that T-V-L peptides and their derivatives can be employed to alleviate the schizophrenic symptoms in mammals afflicted with such symptoms. These polypeptide materials contain the residues of at least three alpha-aminoacids and have the T-V-L structure hereinabove defined. The polypeptide may be an aminoacid, i.e., having one terminal aminoacid moiety in acid form and the other terminal aminoacid moiety in alpha-amino ($-NH_2$) form. It is preferred, however, that the polypeptide materials employed to alleviate the symptoms of schizophrenia contain at least one of its end aminoacid moieties in derivative form, especially the terminal alpha-amino group being acyl-substituted or the terminal carboxylic acid group being in amide or ester form. Preferably both of these terminal moieties are substituted in such manner, and particularly preferred are the acylated amides. These polypeptide materials can also be further substituted, and the pharmaceutically-acceptable, non-toxic derivatives, e.g., acid or base salts, of the polypeptides or their derivative forms can be employed to alleviate the symptoms of schizophrenia in accordance with this invention.

The T-V-L-containing polypeptide materials of the present invention are apparently effective in the treatment of schizophrenic symptoms by causing the alpha-helical configuration of S-protein present in the internal system, e.g., the brain, of the schizophrenic, to assume its randomly-structured form. The polypeptides or acylated polypeptides, esters or amides thereof have the structure:

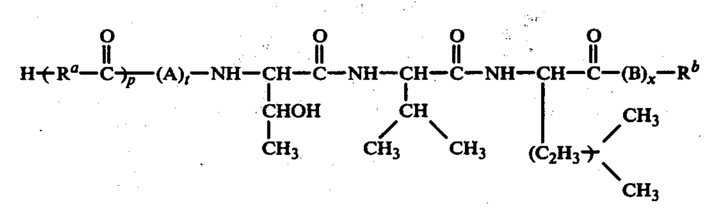

II.

wherein $R^a$ is a saturated aliphatic hydrocarbon group, e.g., alkylene, of 1 to about 20 carbon atoms, preferably lower alkylene, say of 1 to about 4 carbon atoms; $R^b$ is $-O(R^e)$ wherein $R^e$ is hydrogen or a saturated aliphatic hydrocarbon group, e.g., alkyl, of 1 to about 20 carbon atoms, preferably lower alkyl, say of 1 to about 4 carbon atoms, or aryl or aralkyl of 1 to about 4 rings, preferably of 6 to about 24 carbon atoms, or $R^b$ is $-NR^cR^d$ wherein $R^c$ and $R^d$ may be the same or different and may be hydrogen or lower alkyl, e.g., 1 to about 6 carbon atoms or $R^c$ and $R^d$ may be lower alkylene and join to form a cyclic structure including the nitrogen atom to which they are bonded; A and B is each a monoiminoacyl radical, preferably an α-monoiminoacyl radical, containing 2 to about 10 carbon atoms, and B is hydrolyzable from the (L) component of the essential T-V-L structure such that the carboxyl function of the (L)

component is made available in the host; p is 0 or 1; t is from 0 to about 5; x is from 0 to about 5; and t plus x is from 0 to about 5. When t is 2 or more, each A may be the same or different, thus (A)$_t$ may be, for instance, phenylalanylprolyl. Similarly, when x is 2 or more, each B may be the same or different. In a preferred group of compounds, -R$^b$ is -NR$^c$R$^d$ or at least one of p, t or x is other than zero. The (T) component shown in structural formulas above and below may be in either diastereoisomeric form, e.g., as threonyl or allothreonyl wherein the stereochemistry at the β carbon is reversed. Preferably, the (T) component is threonyl. The (L) component in the structural formulas above and below may be

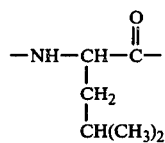

(commonly referred to as leucyl), which is preferred, or in another form such as

—NH—CH—C—
      |    ‖
      CH—CH$_3$   O
      |
      CH$_2$—CH$_3$ as in isoleucyl.

The compounds of this invention include compounds wherein any substituent, e.g., monoiminoacyl radical herein designated by B, on the carboxylic group of the (L) moiety in the essential T-V-L sequence is hydrolyzable. Advantageously, in order to provide the desired activity the substituent is hydrolyzable under the conditions present in the intended environment in a host. Suitable hydrolyzable substituents are those which hydrolyze in the presence of red blood cells at an incubation temperature of about the body temperature of a host, e.g., about 35° to 40° C. One convenient procedure for determining whether or not a substituent is hydrolyzable involves incubating the compound containing the essential T-V-L structure and a substituent on the (L) moiety in a liver medium at about 37° C.

The peptide moieties in the compounds of this invention include peptide moieties which possess optical activity. Various peptide moieties can have configurations designated as L- or D-. The monoiminoacyl radicals comprising A of formula II and the essential T-V-L portion of the compounds may be in the L- or D-form or mixtures thereof such as racemic mixtures. Due to the frequent difficulty in the hydrolysis of D- form peptides which are substituents on carboxyl functions of peptides to preserve the carboxylic function, advantageously the monoiminoacyl radicals comprising B of formula II can have no optical activity or, when optically active, can be in the L-configuration. Among the preferred compounds are those in which (L) of the essential T-V-L sequence is of the D-configuration.

The tripeptide, threonyl-valyl-leucine, or its derivatives described herein, e.g., the corresponding amides, may be obtained in relatively high purity, and may be crystalline, e.g., for instance, at least about 90 or 95 percent pure, preferably substantially 100% pure.

Various compounds of formula II may be intermediates for materials of the formula which are active in the treatment of schizophrenia. For example, when p is zero and R$^e$ is hydrogen, the compound may be an intermediate for the corresponding material in which p is 1 and/or R$^e$ is other than hydrogen. The compounds which are more desired for the treatment of schizophrenia are polypeptides in which p is 0 or 1, and polypeptides containing at least three peptide or aminoacid moieties and t is 0 or more, whether in aminoacid or a derivative form. Polypeptide materials wherein at least one of p, t or x is other than zero may exhibit a longer period of activity than provided by the tripeptide T-V-L in aminoacid form.

Preferred acylated polypeptides for use as active agents or intermediates therefor have the structure:

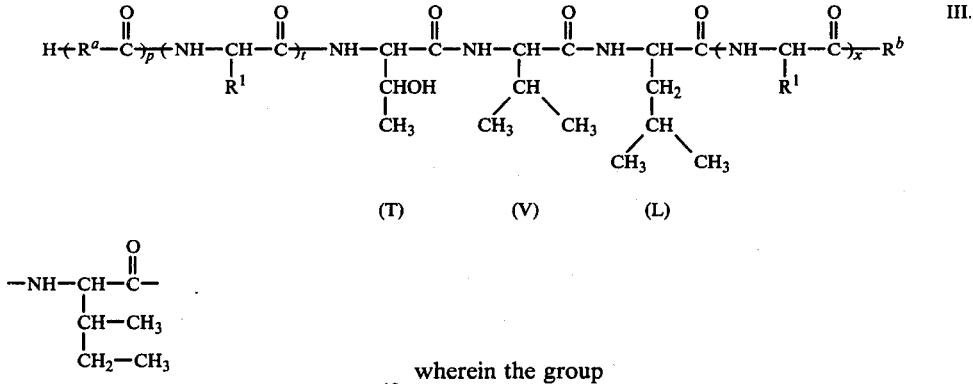

wherein the group

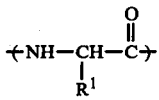

is a monoiminoacyl radical and R$^1$ is, for instance, hydrogen or a lower alkyl group, e.g., of 1 to about 4 carbon atoms, or a

—CH—OR$^2$
   |
   R$^3$ group in which R$^2$ and R$^3$ are hydrogen or lower alkyl, say of 1 to about 4 carbon atoms, or aryl or aralkyl of 1 to about 4 rings, preferably having 6 to about 24 carbon atoms. Such groups may be substituted as in the case of, for example, tyrosyl. The letters R$^a$, R$^b$, p, t, and x have the same meaning as in formula II.

In the compounds illustrated by formula III, R$^1$ is part of an alpha-aminoacid or peptide moiety or residue as in the case of, for instance, threonyl or allothreonyl in which R$^1$ is an alpha-hydroxyethyl group, leucyl in which R$^1$ is a 2-methylpropyl group, valyl in which R$^1$ is an isopropyl group, seryl in which R$^1$ is a hydroxymethyl group, isoleucyl in which R$^1$ is a 1-methylpropyl group, glycyl in which R$^1$ is hydrogen, or alpha-alanyl in which R$^1$ is methyl, arginyl in which R$^1$ is

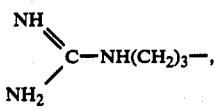

tyrosyl in which R¹ is

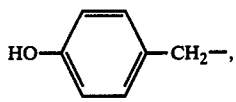

and the like. When the group including R¹ has an alpha-hydroxy group it may be converted to a lower alkoxy or aryloxy group, preferably benzyloxy or t-butyloxy. This may be done during synthesis to protect the hydroxyl function. The peptide moieties, i.e., monoiminoacyl radicals, attached to the essential T-V-L structure may also be prolyl, arginyl, and the like. Also these moieties may be a dicarboxylic acid moiety such as a residue from glutamic or aspartic acid.

The $R^a$ group in the compounds described herein may have up to about 20 carbon atoms, although it is desirable that it be alkylene of up to about 4 carbon atoms. Thus, the N-acyl group

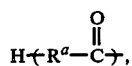

may be, for example, acetyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, palmitoyl, heptadecanoyl, stearyl, and the like. The ester group, $R^e$, may be methyl, ethyl, propyl, butyl, pentyl, hexyl, heptyl, octyl, nonyl, decyl, undecyl, dodecyl, tridecyl, tetradecyl, pentadecyl, heptadecyl, octadecyl, phenyl, benzyl, tertiary butoxycarbonyl, tertiary butyl, dihydro-epi-hydroxyandrosteronyl, and the like. Preferably, the N-acyl group and the ester group are normal and thus have straight carbon to carbon chains. The compounds of the formulae or their precursor intermediates may have substituent groups which do not interfere with the desired chemical or pharmacological activity of the materials.

Intermediates for preparing active compounds of this invention include compounds of the formula

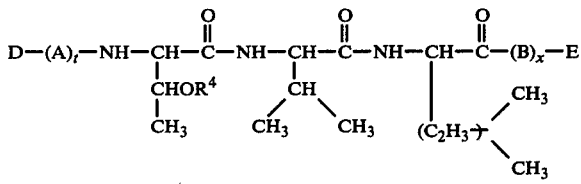   IV.

wherein t, x, A and B are as defined above; D is H or an α-amino protecting group; E is -OH; a terminal carboxylic protecting group; a complex of metal, for instance, zinc, copper, nickel, cobalt, iron, magnesium, or aluminum, the complex preferably being a metal hydroxide complex; or an acid or base addition salt; R⁴ is H, aliphatic hydrocarbon, preferably saturated, e.g., alkyl of 1 to about 20 carbon atoms such as lower alkyl of say 1 to 4 carbon atoms, or araliphatic or aryl of 1 to about 4 rings, preferably of 6 to about 24 carbon atoms; acyl including alkanoyl or aralkanoyl of 1 to about 20 carbon atoms, preferably lower acyclic acyl of 1 to about 4 carbon atoms; tetrahydropyranyl; a monovalent metal such as an alkali metal, e.g., sodium; and the like. A metal such as zinc, copper, nickel, cobalt, iron, magnesium or aluminum may form a complex with functions of the polypeptide such as a carbonylic function.

The α-amino protecting groups may be (1) acyl or thioacyl type, preferably of 2 to about 21 carbons, for example, lower aliphatic acyl of 2 to about 7 carbons, e.g., acetyl, etc.; lower araliphatic acyl of 8 to about 15 carbon atoms such as phthalyl, naphthoyl, benzoyl, etc.; trifluoroacetyl; chloroacetyl; γ-chlorobutyryl; toluenesulfonyl; benzenesulfonyl; nitrophenylsulfenyl; tritylsulfenyl; o-nitrophenoxyacetyl; and the like; (2) aromatic urethane type protecting groups illustrated by benzyloxycarbonyl and substituted benzyloxycarbonyl such as p-chlorobenzyloxycarbonyl, carbonyl, p-nitrobenzyloxycarbonyl, p-bromobenzyloxycarbonyl, p-methoxybenzyloxycarbonyl; (3) aliphatic urethane protecting groups illustrated by tert-butyloxycarbonyl, diisopropylmethoxycarbonyl, isopropyloxycarbonyl, ethoxycarbonyl, allyloxycarbonyl; (4) cycloalkyl urethane-type protecting groups illustrated by cyclopentyloxycarbonyl, cyclohexyloxycarbonyl; (5) thio urethane type protecting groups such as phenylthiocarbonyl; (6) alkyl and aralkyl type protecting groups as illustrated by triphenylmethyl (trityl) and benzyl; (7) trialkylsilane groups such as trimethylsilane.

The terminal carboxylic protecting groups may be (1) -OG wherein G is, for instance, an aliphatic moiety preferably having 1 to about 20 carbon atoms, or araliphatic moiety of 1 to about 4 rings, preferably having 6 to about 24 carbons, and providing an ester terminated with a carbon-containing radical; or acyl, e.g., lower acyclic acyl preferably having 1 to about 6 carbons; (2) an amide providing function, e.g., -NH₂, aminoaliphatic or aminoaraliphatic (e.g., monocyclic araliphatic) of 1 to about 10 carbon atoms, thus, the amine may be primary, secondary or tertiary, e.g., -NR$^c$R$^d$ wherein R$^c$ and R$^d$ are as defined above; or (3) an anchoring agent such as

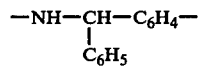

resin support; -O-CH₂-C₆H₄-resin support, chloromethylated resin, hydroxymethyl resin, Merrifield resin, and the like. Preferably, the foregoing aliphatic or araliphatic groups are hydrocarbyl.

The polypeptide materials of this invention, e.g., compounds of formula II, can be employed to relieve the symptoms of schizophrenia in humans and other mammals, and it is believed this is accomplished by reducing the activity of the S-protein, i.e., by causing a reduction in the degree of alpha-helical conformation of the S-protein in the warm-blooded animal. These active compounds may be effective in counteracting the symptoms of schizophrenia and manifest forms thereof such as anxiety tension states, manic depressive psychosis, etc., when pharmacologically-administered internally to a living animal. THe administration of an active compound of this invention, for instance, mixed with a pharmaceutical carrier may be internal, e.g., may be within the digestive tract and parenteral administration is preferred. The active compound may be in solid or liquid form and may be combined with a pharmaceutically-acceptable carrier as a solid, solution, suspension, emulsion or other form. Parenteral administration may be by, for instance, subcutaneous, intraperitoneal, intravenous, intraarterial, intramuscular, or like, routes. For oral administration, an active compound and a pharmaceutically-acceptable carrier may, for example, take the form of a pill, lozenge, tablet, capsule or a liquid suspension. Exemplary carriers are solids such as lactose, magnesium stearate, calcium stearate, starch, terra alba, dicalcium phosphate, sucrose, talc, stearic acid, gelatin, agar, pectin, or acacia, and liquids such as sesame oil, olive oil, water and the like. An enteric coating, such as cellulose acetate phthalate, may also be used. The compositions of this invention may also include preserving agents, stabilizing agents, wetting agents, emulsifying agents, buffers or salts and the like. The active compounds used in the method of the invention, or compositions containing the same, may be either administered together with or include other physiologically-active materials and/or medicaments, e.g., buffering agents, antacids, sedatives, tranquilizers, analgesics, hormones or the like.

Various dosages of active compounds may be employed depending on the particular active compound employed, the severity of the condition being treated, the mode of administration, the extent of desired effect on the host, e.g., mammal, and the like. Thus, the amount of active compound administered may vary, but is sufficient to relieve schizophrenic symptoms in the mammal to a significant extent. The dosages may generally range from at least about 0.01 mg/kg/day (milligrams per kilogram of body weight of mammal per day), say, up to about 2 or more mg/kg/day, more preferably about 0.1 to 1 mg/kg/day. The treatment may consist of a single daily dose, or the above dosages can be given fractionally at periodic intervals, for example, about 2 to 4 doses of about 0.05 to 0.2 mg/kg may be administered per day. The active compound may be included in time-release formulations whereby the above amounts are made available to the body over an extended time period. The period of activity may be prolonged by incorporating the polypeptides into organic, mostly polymeric compounds, such as gelatin, polyphloretinphosphate, or polyglutamic acid.

The compounds of the invention including those active in the treatment of schizophrenic symptoms or their precursor intermediates, may be synthetically-prepared from individual amino acids or from polypeptides to provide the desired T-V-L peptide series. In one mode of synthesis, amino acid components are reacted in the desired order to obtain the peptide structure, e.g., the amine function of a first amino acid may be condensed with the carboxylic acid function of a second amino acid to provide a dipeptide structure which can be further reacted to obtain the desired structure having 3 to about 8 amino acid units or moieties. To obtain the desired combination of amino acid moieties, it is usually expedient to block the sites on the amino acids which might lead to an undesirable side reaction, for instance, the carboxylic function of a first amino acid reactant with an amine function of a first amino acid or a second amino acid molecule. Blocking can be effected by conventional means. Particularly advantageous blocking groups for the amino function of amino acids are the α-amino protecting groups, for instance, phthalyl, carbobenzyloxy, and t-butyloxycarbonyl groups in that they can be easily attached to the amino group without causing racemization of the amino acid, may be relatively inert to reaction conditions, and may be easily removed from the amino group without adverse effect on the amino acid. These protecting groups may be reacted as the acid halide, e.g., chloride, ester, or acid anhydride, e.g., mixed acid anhydride with alkyl formate, e.g., a lower alkyl formate, of the blocking group. The reaction may proceed at ambient temperatures in an inert, organic liquid solvent such as benzene. Higher or lower temperatures, e.g., about 0° to 50° C. may, however, be employed if desired. The carboxylic function of the amino acid may be blocked by reaction with the amino group of the preceding amino acid in the peptide series or by another susceptible blocking group when the acid is the initial acid in the series.

For purposes of ease of recovery of the amino acid synthesis product after each stage of the reaction, providing the initial or terminal amino acid moiety as a resin ester or resin amide can be quite advantageous. Particularly useful resins are, for instance, benzyhydrilamine resin, chloromethylated resin, Merrifield resin, and hydroxylmethyl resin. The preparation of a benzhydrilamine resin is described by Rivallile, et al., Helv. 54, 2772 (1971), and the preparation of a hydroxymethyl resin is described by Bodanszky et al., Chem. Ind. (London) 38, 1597–98 (1968).

The blocking groups should be stable in the reagent and under the reaction conditions for preparing the peptide. Blocking groups for the terminal carboxylic acid group should be stable under the conditions used for removing the alpha-amino protecting group at each stage of the synthesis. The blocking group should retain its protecting properties, i.e., not be split off, under synthesis conditions, and when removed upon completion of the synthesis the reaction conditions employed should not alter the peptide chain in an undesired manner. The blocking groups may be removed by various conventional methods, depending on the nature of the group to be removed, for example, in the presence of trifluoroacetic acid, or by hydrogenolysis with, for instance, hydrogen and a catalyst such as platinum, palladium or the like, or with hydrogen bromide in glacial acetic acid or trifluoroacetic acid or with anhydrous hydrofluoric acid. The hydrogenolysis medium is preferably essentially anhydrous.

The reaction between an existing peptide unit and a subsequent amino acid can be accomplished by solid phase reaction. In preparing resin esters or amides, the resin support and amino acid may be intimately admixed in an inert organic menstruum, for instance, tetrahydrofuran, dioxane, dimethyl formamide, benzene, ethanol, and the like. The reaction proceeds at ambient temperature, although higher and lower temperatures, e.g., about 0° to 80° C., may be employed if desired. The reaction is usually permited to go essentially to completion to maximize the yield of peptide product having the desired order. The use of substantial excesses of amino acid reactant, e.g., at least about 1.5 to about 200 or more times the amount required for reaction on a stoichiometric basis, and substantial reaction times, e.g., at least about 1 hour, preferably at least about 5 hours to 500 or more hours, enhance the completion of the reaction. The degree of completion of the reaction may be determined by the Kaiser color reaction. A positive reaction to Kaiser color reaction indicates unsubstituted sites on the amino acid. A Dorman titration may also be employed to determine completion of the reaction.

Suitable linking methods to provide the polypeptide chain of the compounds of this invention are described in the literature. In general, the amino acid and/or peptide fragments are linked so that, for example, an amino acid or peptide containing a protected alpha-amino group and a terminal carboxyl group is reacted with an amino acid or peptide containing a free alpha-amino group and a protected terminal carboxyl group, or an amino acid or peptide containing an active alpha-amino group and a protected terminal carboxylic group is reacted with an amino acid or a peptide containing a free terminal carboxylic acid and a protected alpha-amino group. The carboxylic group can be activated for instance by conversion into an acid azide, anhydride or imidazolide or into an activated ester such as cyanoethyl ester, thiophenyl ester, p-nitrothiophenyl ester, thiocresyl, p-methanesulfonylphenyl, p-nitrophenyl, 2,4-dinitrophenyl, 2,4,5- or 2,4,6-trichlorophenyl, pentachlorophenyl, N-hydroxysuccinimide, N-hydroxyphthalimide, 8-hydroxyquinoline, N-hydroxypiperidine ester, or by reaction with a carbodiimide (optionally with addition of N-hydroxysuccinimide) or N,N'-carbonyldiimidazole or an isoxazolium salt, for example, Woodward's reagent, the amino group for instance by reaction with a phosphite. Frequently used methods include the carbodiimide method, the Weygand-Wuensch method (carbodiimide in the presence of N-hydroxysuccinimide), the azide method, the method of the activated esters and the anhydride method, also the Merrifield method and the method of the N-carboxyanhydrides or N-thiocarboxyanhydrides.

Conveniently, the carbodiimide method may be employed, the carbodiimide coupling agent may be, for instance, N-ethyl-N'-(γ-dimethylaminopropyl carbodiimide) or a dihydrocarbyl-carbodiimide, e.g., dialkyl of 1 to about 20 carbons, for instance, dicyclohexyl carbodiimide. The carbodiimide may be provided in an inert solvent, for instance, methylene chloride, to assist in handling. Frequently, the mole ratio of carbodiimide to moles of the least abundant amino acid reactant is about 0.9:1 to 10:1. The linking reaction may be conducted in an inert medium, e.g., dichloromethane, in solvent-providing quantities, for instance, at least about 1 to about 100 or more milliliters per gram of amino acid. The reaction proceds at ambient temperature, although higher and lower temperatures, e.g., about −30° to 50° C., may be employed if desired.

The unblocking of an amino acid or peptide fragment for further reaction may be conducted in any convenient manner, and such methods are well known. Advantageously, blocking agents on amino groups, e.g., acyl blocking groups may be removed in a two stage process, using a hydrogen halide, for instance, hydrogen chloride, in each stage. The resultant product is the acid addition salt, e.g., hydrogen chloride salt, which may be neutralized with a base, for instance, triethylamine, pyridine, sodium or potassium hydroxide, sodium or potassium carbonate, or the like. The hydrogen halide may be prepared by bubbling the hydrogen halide into a liquid medium, for instance, dioxane or methylene chloride. A resin ester may be converted to an unblocked peptide by bubbling hydrogen halide, e.g., hydrogen bromide, gas through a medium containing the peptide resin ester and trifluoroacetic acid.

As noted above, it is desirable to modify the polypeptide containing the T-V-L linkage to provide a compound which exhibits a longer effective life in treating schizophrenic symptoms than the aminoacid tripeptide, and thus, the latter polypeptide may be converted to an omega-N-acylated polypeptide. Known acylation procedures can be employed although it may be most desired to use a procedure which does not disturb the optical activity of the amino acid moieties. The alpha-amino group of the polypeptide may be acylated by reaction with the corresponding acid halide, e.g., acid halide, acid anhydride, or the like, using conventional methods. The terminal carboxylic acid or ester group may be esterified or transesterified in accordance with conventional procedures to provide a peptide which may exhibit a larger effective dose. Esterification can be effected by reaction of the polypeptide having an unblocked, terminal carboxylic function with the corresponding alcohol. The amides having the characteristic T-V-L linkage of the compositions of this invention may be prepared in accordance with known procedures. For instance, the corresponding acid or acid halide, e.g., chloride, of the peptide may be reacted with ammonia or a primary or secondary amine. The ammonia or amine is often provided in at least a stoichiometric amount for complete reaction with the peptide structure. The reaction may be conducted in an inert solvent such as tetrahydrofuran and may conveniently be at a temperature of about 10° to 50° C. or more. Generally, the higher the molecular weight of the acyl and ester groups on the polypeptide the slower and more prolonged will be its effect in treating schizophrenic symptoms.

The functional derivatives of the compounds and intermediates of this invention include the pharmaceutically-acceptable, salts, including acid and base addition salts, of the polypeptides. The acid addition salts can be obtained by reacting the polypeptide with an organic or inorganic acid, such as hydrochloric acid, hydrobromic acid, sulfuric acid, phosphoric acid, acetic acid, maleic acid, tartaric acid, citric acid, malic acid, ascorbic acid, benzoic acid, and the like. The compounds having the T-V-L linkage may also be in the form of metal complexes prepared by contacting the polypeptides with a sparingly-soluble salt, hydroxide or oxide of metal. Metals which may be employed include cobalt, copper, calcium, iron, zinc, magnesium, sodium, potassium and ammonium. Other metals which may be employed include nickel and aluminum. Thus, for example, a metal complex can be obtained by adding the polypeptide and a sparsely-soluble, metal salt, metal hydroxide, or metal oxide to an aqueous medium, or by adding an alkaline medium to an aqueous solution of the polypeptide and an essentially insoluble metal salt to form an insoluble polypeptide-metal hydroxide complex. An insoluble polypeptide-metal salt complex can also be prepared in situ by adding to an aqueous alkaline medium the polypeptide and a metal salt.

The invention will be described further by the following examples. In the examples, the peptide moieties having optical activity are in the L- configuration unless otherwise stated.

EXAMPLE 1

Preparation of Leucine Benzyl Ester p-Toluenesulfonate

In a 200 ml 3 neck flask equipped with a Dean and Stark trap, reflux condenser (with drying tube attached), and mechanical stirrer, 15 grams (0.0789 mole) of p-toluenesulfonic acid monohydrate is refluxed until one equivalent of water is released. At this point 10 grams (0.07634 mole) leucine and 17.0 grams (0.15 mole) benzyl alcohol are added. The mixture is refluxed for 4 hours and allowed to cool to room temperature. The solvents are removed in vacuo and a white, solid residue is produced. The white solid is washed with anhydrous ether and recrystallized from ethanol/ether to yield in three crops 28.2 grams of leucine benzyl ester p-toluene sulfonate (94% yield) having a melting point of 157°–158° C. (with decomposition).

EXAMPLE 2

Preparation of Benzyl N-α-t-Butyloxycarbonylvalylleucinate

Approximately 13.2 grams (0.0336 mole) of benzyl leucinate p-toluenesulfonate is treated with sodium bicarbonate to provide benzyl leucinate, which is recovered by methylene chloride extraction. In a 200 ml 3 neck flask equipped with a nitrogen gas inlet and outlet adaptors and a magnetic stirrer, 6.25 grams (0.34 mole) of dicyclohexylcarbodiimide is dissolved in 30 milliliters of freshly distilled dry $CH_2Cl_2$, and the recovered benzyl leucinate is added thereto. The mixture is maintained under a nitrogen atmosphere and is cooled to approximately $-30°$ C. using dry ice and carbon tetrachloride. To the mixture 7.45 grams (0.0336 mole) of N-α-t-butyloxycarbonylvaline dissolved in 50 ml of dry $CH_2Cl_2$ is added dropwise. The resulting mixture is stored at $-10°$ C. for 2 days. After removing a resultant white precipitate by filtration, the methylene chloride layer is washed successively with 25 percent aqueous acetic acid, aqueous sodium bicarbonate solution, water, and saturated aqueous saline solution. The organic layer is then dried over anhydrous $MgSO_4$ and the solvent is removed in vacuo. The residue is taken up in ethyl acetate, filtered, and again concentrated in vacuo. The resulting white solid is recrystallized from ethanol/hexane to yield in two crops 9.17 grams of benzyl N-α-t-butyloxycarbonylvalylleucinate (65% yield) having a melting point of 90°–91° C.

EXAMPLE 3

Preparation of Benzyl N-α-t-Butyloxycarbonyl-O-benzylthreonylvalylleucinate.

In a 100 ml 3 neck flask equipped with gas inlet and outlet adaptors and magnetic stirrer, 4.08 grams (0.00972 mole) of benzyl N-α-t-butyloxycarbonylvalylleucinate is dissolved in 50 milliliters of glacial acetic acid. The mixture is cooled to 5° C. and hydrogen chloride gas is bubbled through the mixture for 30 minutes. The mixture is then taken to dryness in vacuo. The resulting white powder, benzyl valylleucinehydrochloride, is repeatedly washed with anhydrous ether. The powder is suspended in 30 milliliters of dry $CH_2Cl_2$, cooled to $-30°$ C., and treated with 1.38 milliliters (0.010 mole) of triethylamine and stirred for 30 minutes to provide a solution.

The resulting triethylamine solution is then added to 1.94 grams (0.010 mole) of dicyclohexylcarbodiimide dissolved in 30 milliliters of freshly distilled, dry $CH_2Cl_2$. This solution is maintained under a nitrogen atmosphere and 3.0 grams (0.00972 mole) of N-α-t-butyloxycarbonyl-O-benzylthreonine dissolved in 30 milliliters dry $CH_2Cl_2$ is added dropwise. The reaction mixture is kept at $-10°$ C. for two days. The resulting white precipitate is removed by filtration, and the methylene chloride layer is successively washed with water, 25% aqueous acetic acid, aqueous sodium bicarbonate solution, water, and saturated aqueous saline solution. The organic layer is dried over anhydrous $MgSO_4$ and the solvent is removed in vacuo. The residue is taken up in ethyl acetate, filtered, and concentrated in vacuo to yield 3.56 grams of a white powder which is benzyl N-α-t-butyloxycarbonyl-O-benzylthreonylvalylleucinate (60% yield, m.p. 115° to 119° C.).

EXAMPLE 4

Preparation of Benzyl O-Benzylthreonylvalylleucinate Hydrochloride.

Hydrogen chloride gas is slowly bubbled for 50 minutes through a cold (5° C.) and stirred solution of 4.1 grams (6.71 m mole) of benzyl N-α-t-butyloxycarbonyl-O-benzyl-threonylvalylleucinate in 50 milliliters of glacial acetic acid. The solvent is removed in vacuo. The residue is washed with ether and recrystallized from ethanol/ether to yield 3.14 grams of benzyl O-benzylthreonylvalylleucinate hydrochloride (86% yield) having a melting point of 200°–202.5° C.

EXAMPLE 5

Preparation of Threonyl-Valyl-Leucine

One gram of benzyl O-benzylthreonylvalylleucinate hydrochloride is neutralized to provide benzyl O-benzylthreonylvalylleucinate. A hydrogenolysis mixture is prepared containing the benzyl O-benzylthreonylvalylleucinate, 0.5 grams of 10 percent palladium on charcoal per 0.01 mole of the material to be hydrogenated, and absolute ethanol. To the mixture is added 1.1 mole equivalents of acetic acid based on the benzyl ester. The mixture is hydrogenated for 4 hours. The catalyst is removed by filtration and the solvents are removed in vacuo. The residue is washed with anhydrous ether and recrystallized from an ethanol/ether mixture to provide 544 milligrams of the free peptide, threonylvalylleucine (85% yield).

EXAMPLE 6

Preparation of Benzyl N-α-Acetyl-O-benzylthreonylvalylleucinate.

Benzyl O-benzylthreonylvalylleucinate is prepared from 1 gram of benzyl O-benzylthreonylvalylleucinate hydrochloride as in Example 5 and is dissolved in acetic acid, and 2 equivalents acetic anhydride based on the benzyl ester are added. The mixture is stirred overnight. The solvents are evacuated in vacuo. The residue is recrystallized from methanol/ether, to yield 806 milligrams of benzyl N-α-acetyl-O-benzylthreonylvalylleucinate (85% yield).

EXAMPLE 7

Preparation of N-α-acetylthreonylvalylleucinamide

One gram of benzyl N-α-acetyl-O-benzylthreonylvalylleucinate is dissolved in 95% ethanol. Ammonia is bubbled through the solution for 8 hours. After stirring at room temperature for 48 hours, the solvents are removed in vacuo. The residue is washed with ether to yield 795 milligrams (99%) of N-α-acetyl-O-benzyl-threonylvalylleucinamide. One gram of the N-α-acetyl-O-benzylthreonylvalylleucinamide is subjected to hydrogenolysis in absolute ethanol to yield 705 milligrams (90% yield) of N-α-acetylthreonylvalylleucinamide.

EXAMPLE 8

Merrifield Synthesis of Threonyl-valyl-leucine

A solution of 5.3 grams of t-butyloxycarbonyl-L-leucine (21.2 mmole), 2.5 milliliters of triethylamine (18 mmole) in a 2-methyltetrahydrofuran solvent is prepared and 20 grams of Merrifield resin, which is polystyrene cross-linked with 2% divinylbenzene, providing 21.2 mmole of chlorine is added there to. The Merrifield resin is analyzed to contain about 1.06 mmole of chlorine per gram of resin, and prior to use, the resin is washed with methanol, distilled water, ethanol, and methylene chloride and then dried in vacuo at 100° C. Prior to use the 2-methyltetrahydrofuran is distilled over a sodium dispersion, and the triethylamine is distilled over phenylisocyanate and then redistilled over a sodium dispersion. The mixture is refluxed for approximately 70 hours to effect esterification of the blocked aminoacids to the resin. After the esterification reaction, the resin is washed with tetrahydrofuran, ethanol, glacial acetic acid, ethanol, distilled water, ethanol, and methylene chloride, and then dried in vacuo at 100° C. for three hours. Approximately 21.5-22 grams of t-butyloxycarbonyl-L-leucine resin ester is obtained.

The t-butyloxycarbonyl-L-leucine resin ester is suspended in 200 milliliters of methylene chloride and stirred by bubbling high purity nitrogen through the suspension. The t-butyloxycarbonyl protecting group is removed by adding 400 milliliters of an equal volume mixture of trifluoroacetic acid and methylene chloride. The resin is washed and then neutralized using 400 milliliters of 10% by volume triethylamine in chloroform. The resin is washed with chloroform and methylene chloride. About 4.82 grams of t-butyloxycarbonyl-L-valine is added to the resin followed by an equivalent amount, i.e., about 4.57 grams, of dicyclohexylcarbodiimide, (24 mmole), and the coupling reaction is allowed to proceed for at least 16 hours. The resultant t-butyloxycarbonyl-L-valyl-L-leucyl resin ester is then washed with methylene chloride, essentially anhydrous ethanol, glacial acetic acid, ethanol, and methylene chloride to remove the dicyclohexylurea by-product. The completeness of the reaction is checked by Kaiser color reaction.

Essentially the same procedure as described above is employed to remove the t-butyloxycarbonyl (boc) protecting group. To the unblocked resin ester is added 5.00 grams of t-boc-O-benzyl-L-threonine then an equivalent amount (i.e., 3.6 grams) of dicyclohexylcarbodiimide (18.4 mmole) is added, and the coupling reaction is allowed to proceed for four hours. The resultant resin ester is washed in essentially the same manner as described above and then dried overnight at room temperature in vacuo over phosphorus pentoxide. Approximately 22-23 grams of t-butyloxycarbonyl-O-benzyl-L-threonyl-L-valyl-L-leucyl resin ester is obtained.

Cleavage of the tripeptide from the resin is effected by suspending the dried t-butyloxycarbonyl-O-benzyl-threonylvalylleucine resin ester in 100 milliliters of 100% trifluoroacetic acid through which anhydrous hydrogen bromide is bubbled. During this process the resin ester linkage and simultaneously the O-benzyl protecting group on threonine are cleaved, yielding the soluble hydrobromide and trifluoroacetate salts of threonylvalylleucine in trifluoroacetic acid.

The trifluoroacetic acid solution is then evaporated to dryness, and the residue is dissolved in 100 milliliters of an equal volume mixture of methanol-distilled water. The mixture is taken to dryness under reduced pressure, and the residue is dissolved in 100 milliliters of ethanol, and again recovered by drying under reduced pressure. The dried material is then dissolved in 10 to 20 milliliters of a minimum of 30% glacial acetic acid and filtered. Solid sodium carbonate or sodium bicarbonate is slowly added until precipitation occurs. The final tripeptide product is recrystallized from ethanol/water or by dissolving the product in a large excess of distilled water, concentrating the solution by distilling off some of the water, and allowing crystal formation to occur at refrigerator temperature, about 5° C. About 657 milligrams of L-threonyl-L-valyl-L-leucine (75% yield) having a melting point range of 240°-242° C. (with decomposition) is obtained.

EXAMPLE 9

Preparation of L-threonyl-L-valyl-D-leucine

The procedure of Example 8 is essentially repeated except that D-leucine is employed instead of L-leucine and L-threonyl-L-valyl-D-leucine is prepared. The product is a white crystalline mixture which is observed to have a decomposition point of about 240° C. with charring.

EXAMPLE 10

Preparation of N-α-Acetyl-threonyvalylleucine t-Butyloxycarbonyl-O-benzylthreonylvalylleucine resin ester is prepared in essentially the same manner as disclosed in Example 8. The t-butyloxycarbonyl protecting group is removed in essentially the same manner the groups on the leucyl resin ester and valylleucyl resin ester are removed in Example 8, to provide O-benzyl-threonylvalylleucine resin ester. About 5.0 grams of dried O-benzylthreonylvalylleucine resin ester is acetylated by first washing the resin ester with dimethylformamide, and then reacting the resin with the acetylation reagent comprising 100 milliliters of 44 parts by volume dimethylformamide, 5 parts by volume acetic anhydride, and 1 part by volume triethylamine for 20-50 minutes and the resin is washed with dimethylformamide, followed by methylene chloride, and then dried under vacuum at room temperature overnight.

The N-acetyl peptide is cleaved from the resin in a manner essentially the same as described in Example 8. The trifluoroacetic acid solution is then evaporated to dryness under reduced pressure. The residue is washed with an equal volume mixture of methanol and water, recovered by evaporating to dryness under reduced pressure, washed with ethanol, and again recovered by evaporating to dryness under reduced pressure. The final product is then recrystallized from ethanol-ether, providing 400 milligrams of N-α-acetyl-threonylvalyl-leucine (55% yield) having a melting point range of 210°-214° C. (with decomposition).

EXAMPLE 11

Merrifield Synthesis of the Hydrochloride Salt Of Glycylthreonylvalylleucine

Starting with 10 grams of O-benzylthreonylvalylleucine resin ester as prepared in a manner essentially the same as that disclosed in Example 10, the coupling of t-butyloxycarbonyl-glycine is accomplished by suspending the resin ester in 100 milliliters of methylene chloride, adding 1.94 grams of t-butyloxycarbonylglycine (10 mmole), followed by an equimolar amount, i.e., 2.06 grams, of dicyclohexylcarbodiimide (10 mmole) and allowing the condensation reaction to proceed for four hours. The t-glycylbutyloxycarbonyl-O-benzylthreonyl valylleucine resin ester is cleaved from the resin in essentially the same manner as previously described in Example 8. After appropriate washings with methanol, distilled water, ethanol, and addition of sodium carbonate to attain a pH of 4.5, the product is taken down to dryness under reduced pressure.

The glycylthreonylvalylleucine product is converted to its hydrochloride salt by dissolving it in 100 milliliters of a mixture of 3 parts by volume of ethanol to one part by volume ether and bubbling anhydrous hydrogen chloride gas through the solution for approximately 10 minutes. The product is filtered and dried overnight at room temperature in a vacuum dessicator to provide 600 milligrams of the hydrochloride salt of glycylthreonylvalyllleucine (60% yield) having a melting point range of 225°–226° C. (with decomposition).

EXAMPLE 12

Merrifield Synthesis of N-α-Acetyl-tyrosyl-threonylvalylleucine

O-Benzyl threonylvalylleucine resin ester (prepared essentially as described in Example 10) in an amount of 7.4 grams is added to a reaction flask and suspended in 75 milliliters of methylene chloride. To the suspension is then added 3.735 grams of t-butyloxycarbonyl-O-benzyltyrosine (10 mmole), followed by an equivalent amount of dicyclohexylcarbodiimide (2.06 grams, 10 mmole), and the coupling reaction is allowed to proceed for four hours. Stirring is accomplished by bubbling high purity nitrogen through the suspension. The resin is then washed with methylene chloride, ethanol, acetic acid, ethanol and methylene chloride to remove the dicyclohexylurea byproduct, and then dried overnight at room temperature in vacuo over phosphorous pentoxide. The dried product, O-benzyltyrosyl-O-benzylthreonylvalylleucine resin ester, typically increases in weight to 7.50–7.55 grams.

The N-acetylation is carried out essentially by the process described in Example 10 for the synthesis of N-α-acetyl-threonylvalylleucine except that 7.5 milliliters of acetic anhydride, 2.5 milliliters of triethylamine and 50 milliliters of dimethylformamide are employed. After the N acetylation, the resin is washed with dimethylformamide, followed by methylene chloride and dried under vacuum at room temperature overnight.

The cleavage of the peptide from the Merrifield resin is conducted in essentially the same manner as disclosed in Example 8 except to avoid possible electrophilic aromatic substitution on the tyrosine ring by bromine, the hydrogen bromide is first passed through a resorcinol-trifluoroacetic acid mixture in a ratio of 2 grams resorcinol per 100 milliliters of trifluoroacetic acid to remove traces of $Br_2$. As an added precaution against electrophilic substitution, 20 milliliters of anisole are added directly to the cleavage vessel. The final product, N-α-acetyl-tyrosylthreonylvalyllleucine, is recrystalized from ethanol-ether providing 900 milligrams of the tetrapeptide (59% yield) having a melting point range of 234.5°–235° C. (with decomposition). Amino acid analysis of the product provides 0.93 tyrosine, 1.00 threonine, 1.00 valine, and 1.00 leucine.

EXAMPLE 13

Merrifield Synthesis of Threonylvalylisoleucine

A solution of 5.3 grams of t-butyloxycarbonyl-L-isoleucine (21.2 mmole), 2.5 milliliters of triethylamine (18 mmole) in a 2-methyltetrahydrofuran solvent is prepared and 20 grams of Merrifield resin is added thereto. Prior to use, the resin is washed with methanol, distilled water, ethanol, and methylene chloride and then dried in vacuo at 100° C. Prior to use, the 2-methyltetrahydrofuran is distilled over a sodium dispersion, and the triethylamine is distilled over phenylisocyanate and then redistilled over a sodium dispersion. The mixture is refluxed for approximately 72 hours to effect esterification of the blocked amino acids to the resin. After the esterification reaction, the resin is washed with tetrahydrofuran, ethanol, glacial acetic acid, ethanol, distilled water, ethanol, and methylene chloride, and then dried in vacuo at 100° C. for three hours. Approximately 21.5–22 grams of t-butyloxycarbonyl-L-isoleucine resin ester is obtained. This coupling of the t-butyloxycarbonylvaline to the t-butyloxycarbonylisoleucine resin ester is performed in essentially the same manner as the coupling of t-butyloxycarbonyl-L-valine to the t-butyloxycarbonyl-L-isoleucine resin ester disclosed in Example 8. However, because of the even greater steric hindrance, the reaction is allowed to proceed for 24 hours. The resin is then washed as usual to remove by-products and completeness of the reaction is checked by the Kaiser color reaction. The addition to t-butyloxycarbonyl-threonine to obtain t-butyloxycarbonyl-threonylvalylisoleucine resin ester, the cleavage of the peptide from the resin to obtain t-butyloxycarbonyl-threonylvalylisoleucine, and its subsequent isolation and purification are performed in essentially the same manner as in the preparation of threonylvalylleucine disclosed in Example 8. The tripeptide, threonylvalylisoleucine, is obtained in an amount of about 600 milligrams (68% yield).

EXAMPLE 14

Merrifield Synthesis of Threonylvalylleucylarginine

Essentially the same procedure as in Example 8 is followed except employing 6.78 grams of t-butyloxycarbonylnitro(guanidinyl)-L-arginine (21.2 mmole) as the amino acid esterified to 20 grams of the Merrifield resin. The esterification is conducted by refluxing the mixture for about 72 hours and the resin ester is washed and dried as in Example 8 to provide about 22 or 23 grams of t-butyloxycarbonyl-nitroarginine resin ester. About 5 grams of t-butyloxycarbonyl-L-leucine (24 mmole) is coupled to the nitroarginine resin ester by the addition of an equivalent amount of dicylohexylcarbodiimide (4.6 grams, 24 mmole), allowing the reaction to proceed for 16 hours. After the resin ester is washed, the coupling of t-butyloxycarbonyl-L-valine and t-butyloxycarbonyl-O-benzyl-L-threonine to the resin ester is conducted by essentially the same procedure as previously described in Example 8. Approximately 24 grams of t-butyloxycarbonyl-O-benzoyl-L-threonyl-L-valyl-L-leucyl-arginine resin ester is obtained.

Because of the stability of the nitro group to hydrogen bromide, the protected peptide resin ester is cleaved with anhydrous hydrogen fluoride in order to also effect removal of the nitro group. After passage through an appropriate ion-exchange resin, the eluant is concentrated down to an oil and then isoelectrically precipitated by the addition of solid sodium carbonate. The product, L-threonyl-L-valyl-L-leucyl-L-arginine, is recrystallized from an ethanol-water solution yielding approximately 900 milligrams of the tetrapeptide.

Peptides having the characteristic T-V-L structure may also be prepared using a solid phase reaction with chloromethylated resin which is a polystyrene cross-linked with divinylbenzene resin and is commercially available from Bio Rad Laboratories, Richmond, California, under the trade name of Bio Beads SX-1. In these processes for the addition of peptide moieties, for instance, a t-butyloxycarbonylleucine resin ester is suspended in dioxane and unblocked using 4 normal hydrochloric acid. The resultant hydrochloride is neutralized with triethylamine and washed. The coupling of additional amino acid moieties may be conducted using a coupling agent such as dicyclohexyl carbodiimide. This procedure has not been found to be economically attractive as other synthesis procedures, for example, the Merrifield synthesis.

EXAMPLE 15

Threonylvalylleucine Methyl Ester

Crude threonylvalylleucine (0.066 g., 0.2 mmole) is placed in a 5 milliliter reaction vial and is dried at 100° C. under vacuum overnight over phosphoric anhydride desiccant. The dried tripeptide is dissolved in 0.54 milliliter of anhydrous methanol. A previously prepared mixture of dimethoxypropane and reagent grade hydrogen chloride in a weight ratio of 542:83 is added in an amount of 0.63 milliliter to the reaction mixture. The reaction vial is tightly sealed. The mixture is thoroughly mixed and then is allowed to stand over night to provide the threonylvalylleucine methyl ester. The solvents are then removed by evaporation under a stream of nitrogen, followed by vacuum drying the ester at 100° C. over phosphoric anhydride desiccant overnight.

EXAMPLE 16

N-O-diacetyl-Threonylvalylleucine Methyl Ester

The product of Example 15 is dissolved in 0.38 milliliter of pyridine. Acetic anhydride in the amount of 0.1 milliliter (2 m. mol.) is added as the acylation agent and the reaction mixture is maintained at 37° C. for 20 minutes in a tightly closed vial. The solvent is removed from the acylated product by evaporation under a stream of dry nitrogen, followed by vacuum drying at 100° C. over phosphoric anhydride desiccant overnight.

The acylated tripeptide ester N-O-diacetyl-threonyl-valylleucine-methyl ester can be purified by dissolving the crude product in methanol and passing the sample through a high pressure, liquid chromatograph operation. A Waters modular liquid chromatograph equipped with a 10 feet by ⅜ inch diameter preparative column packed with Phenylporasil-B ® is employed using methanol as the eluent. The elution is monitored for changes in refractive index and UV absorbance at 225 nm. the flow rate of the methanol eluent is 1 milliliter per minute. The major peak with a retention volume of approximately 100 milliliters is collected as the purified fraction. The solvent from this fraction is removed by evaporation under a stream of dry nitrogen followed by vacuum drying at 100° C. over phosphoric anhydride desiccant overnight.

The following example illustrates the isolation and production of the tripeptide threonylvalylleucine from animal sources.

EXAMPLE 17

Extraction and Isolation of Threonylvalyl-Leucine-Containing Polypeptide From Beef Brain The hypothalami from several beef brains are dissected out and homogenized in buffer solution, hereinafter referred to as "tris citrate buffer", which has been prepared as follows:

Tris Citrate Buffer

A 0.498 molar aqueous solution of tris citrate buffer is prepared as follows. To 1 liter of distilled water is added 9.58 grams of the citric acid and 49.9 grams tris(hydroxymethyl)-aminomethane. The pH of the resulting solution is adjusted to 8.65 by the addition of 0.1 molar aqueous solution of sodium hydroxide.

Homogenization of the hypothalami is conducted in four parts by volume (milliliters) of the tris citrate buffer per each part by weight (grams) of hypothalami. The homogenized mixture is centrifuged at 15,000 rpm for 20 minutes at 4° C. and the supernatant liquid, which contains extracted anti-S protein factor together with numerous impurities, is retained.

Four kilograms of starch hydrolysate is washed once with distilled water, then twice with the tris citrate buffer. The wet starch is formed into a block measuring 123 centimeters long by 60 centimeters wide by 5 centimeters thick. The two ends of the block are held in place by filter paper to permit excess buffer to drain out of the block. After such drainage the block has a thickness of only about 1.5 centimeters.

Across the width of the starch block, beginning at a point 43.5 centimeters from one end thereof, is excavated a 1 inch wide section of the block. The temperature of the block is adjusted to 4° C. The anti-S protein factor-containing supernatant liquid from the foregoing centrifugation (measuring about 35–40 ml.) is mixed with 10 drops of bromphenol blue. The resultant solution is mixed with the excavated starch and that mixture is poured into the 1-inch wide trough in the block.

The block is then subjected to an electrophoretic current of 750 volts and 50 milliamperes, the cathode being connected to that end of the block which is 43.5 centimeters distant from the trough, and anode to the other end. The current is continuously passed through the block until the blue line across the width of the block (provided by the presence of the bromphenol blue) moves toward the anode a distance of 42 centimeters. This requires about 18 hours. During this time a bright red line (provided by the hemoglobin that was present in the extract from the hypothalami) moves toward the cathode a distance of about 5 centimeters from the trough.

The area between the blue and red lines after electrophoresis is complete is divided into 10 strips, each strip extending across the width of the block and being about 2 inches wide. Each strip is separately and completely excavated from the block and is slurried in 12 ml. of the tris citrate buffer for about 10 minutes. The slurry is then vacuum filtered through a Buchner funnel. Each of the resultant 10 fractions is assayed according to the tryptophan uptake method described in *Biological Psychiatry*, Vol. 7, No. 1, p. 53, (1973) as an indication of the amount of anti-S protein factor therein. The two or three of the active fractions are retained. Numbering the strips on the starch block from 1 to 10 beginning with that adjacent the blue line, the fractions containing the greatest anti-S protein factor activity are usually those obtained from strips Nos. 2, 9, and 10.

The foregoing procedure is repeated a sufficient number of times to provide 20 fractions having relatively high anti-S protein factor activity. These 20 fractions are then combined and subjected to evaporation through dialysis tubing to reduce the volume from an initial 100–160 ml. to about 40–60 ml.

A packed column for use in chromatographing the concentrated solution of crude anti-S protein factor is prepared as follows:

DEAE Cellulose Column

800 Grams of "Selectacel" brand of DEAE-type cellulose (a diethylaminoethyl cellulose sold by Brown Company of Berlin, New Hampshire) is washed twice with 5 gallon portions of a 0.19 normal aqueous solution of sodium hydroxide. Following that, the packing material is washed with 5 gallon portions of 0.19 normal hydrochloric acid. The material is then washed with 0.005 molar phosphate buffer until chloride-free (usually 25 washes). The packing material is then placed in a 110 centimeter high glass column having an internal diameter of 2.5 centimeters.

The concentrated, crude solution of anti-S protein factor is placed on the DEAE column and the column is then eluted using a 2 flask gradient elution system in which flask A contains 1,000 ml. of 0.005 molar aqueous cation phosphate buffer solution (pH 7.4) and flask B contains 1,000 ml. of 0.04 molar aqueous cation phosphate buffer solution (pH 4.3) which has been augmented with sodium chloride in a ratio of 405.5 grams of sodium chloride per 50 liters of buffer solution. The eluate is collected in 15 ml. fractions, numbering about 120 in all. Each fraction is assayed for anti-S protein factor activity by the tryptophan uptake method and the 10 fractions having the greatest anti-S factor activity are combined and concentrated by lyophilization to about 10 percent of their original volume.

The entire foregoing procedure is repeated a sufficient number of times to provide enough anti-S protein factor-containing concentrate to show a total protein content of about 200 milligrams as determined by the Lowry method. This will require about 300–400 ml. of concentrate, in turn requiring about 400–1,000 grams of beef hypothalamus, in turn requiring about 160 head of cattle.

The concentrate containing about 200 milligrams of protein is dialyzed against distilled water for 24 hours. For every 17 ml. of the concentrate, 4.25 ml. of 0.1 molar trypsin and 2.1 ml. of 1 molar $CaCl_2$ is added. The pH of the entire mixture is adjusted to 7.8 with 1 molar NaOH and then incubated for two hours in a waterbath shaker at 37° C. After incubation, the solution is filtered through a 10,000 molecular weight Diaflo membrane (Amicon UM-10). After filtration, 4.25 ml. of 0.1 molar pepsin solution is added per 17 ml. of the filtrate mixture. The pH is adjusted to 1.5 with 1 molar HCl and the mixture is incubated again for two hours at 37° C. After incubation, the pH is raised to 7.8 with 1 molar NaOH and the solution is filtered through a 1,000 molecular weight Diaflo membrane (Amicon UM-2).

The filtrate is subjected to flash evaporation to reduce its volume to about 50 ml. The resulting mixture is centrifuged, and the supernatant liquid retained. The pH of the supernatant liquid is adjusted to below 2.2 by the addition of concentrated hydrochloric acid. The acidified liquid is then diluted with distilled water to a volume of 75 ml. This anti-S protein factor-containing solution is then subjected to column chromatography on a column prepared as follows:

First Sulphonated Resin Column

The packing material employed is "Aminex 50-WX2" brand by Bio Rad Company, which is a hydrogen ion form of "Dowex" cation exchange resin having a particle size of 200–325 mesh. The resin is a sulphonated polystyrene having 2 percent nominal cross-linking by divinylbenzene. The packing material is washed in a Buchner funnel with 0.1 normal hydrochloric acid until the wash is colorless. Next the material is washed with distilled water until the wash exhibits a pH of 5, following which the material is washed with approximately 3 volumes of 2.0 normal aqueous solution of sodium hydroxide. Again the material is washed with distilled water until the wash has a pH of 5. The packing material is then transferred to a beaker and slurried in two volumes of 1 normal aqueous solution of sodium hydroxide at 35° C. for 2–3 hours. The resultant slurry is then filtered through a Buchner funnel and the filter cake washed with distilled water until the wash water has a pH of 5. The packing material is then slurried in two volumes of 0.2 molar aqueous solution of sodium citrate (pH 3.1) and the slurry is poured into a glass column 150 centimeters high and 2 centimeters in internal diameter.

The acidic, aqueous solution of crude anti-S protein factor is placed on the Aminex column and the column is then eluted using a 2 flask gradient elution system in which flask A contains 2,000 ml. of 0.2 molar aqueous solution of sodium citrate (pH 3.1) and flask B contains 2,000 ml. of an acetate citrate buffer (pH 9.1) prepared from 315 gram citric acid and 402 gram sodium acetate in 4 liters of deionized water. The column is maintained under 10 psi of nitrogen. The eluate is collected in 10 milliliter fractions, numbering about 120 in all.

The fractions are numbered in the order in which they are taken from the column. Each of the thus-obtained fractions is assayed by the tryptophan uptake method for anti-S protein factor activity. A graph is prepared plotting the numbers of the fraction along the x-axis and the activities of the fractions along the y-axis. At least one peak of activity will be noticed in the resulting graph, usually in the region between the 20th fraction and the 30th fraction, and often other peaks will be observed, e.g., one in the 40's, one in the 70's, one in the 90's, and one in the region between 110 and 120. The fractions which make up each peak, e.g., about 2 or 3 fractions in the 20's, are pooled together for further treatment. Each such pool is thereafter treated separately, in the following manner.

PARTITION CHROMATOGRAPHY

METHOD A

The pool of fractions exhibiting high anti-S protein factor activity is flash evaporated on a rotary evaporator to about 5–10 ml. The resultant concentrate is then subjected to curtain electrophoresis using a Beckman Spinco Model CP, curtain electrophoresis apparatus. 20 Liters of an electrolyte solution is prepared by mixing 22.4 ml. of 0.5 molar aqueous solution of $KH_2PO_4$ with 259.2 ml. of 0.5 molar aqueous solution of $Na_2HPO_4$, diluting the mixture to 20 liters with distilled water, and adjusting the pH of the resulting solution to 8.0 by the addition of either phosphoric acid or sodium hydroxide, whichever is required. 50 Milliamperes of 950 volt direct current is employed. Only about 5 liters of the electrolyte solution is used for each run. The electrophoretically fractionated solution of anti-S protein factor plus impurities is collected from the electrophoresis apparatus in 32 fractions, each having a volume of about 15 ml. Each of these fractions is assayed for anti-S protein factor activity by the tryptophan uptake method. The fractions having the greatest activity are retained and pooled together. This is often the 8th through the 12th fractions taken from the apparatus.

The pool of the most active fractions is subjected to flash evaporation on a rotary evaporator to reduce its volume to about 1–5 ml. The concentrated solution, which now contains as little as about 5 milligrams of polypeptide material, is then subjected to separation using columns of a molecular sieve prepared as follows:

Molecular Sieve Columns

Two glass columns are used in series, each column being 200 centimeters high and 0.81 centimeter in internal diameter. Both columns are packed with "Sephadex G-15 fine" brand of molecular sieve material supplied by Pharmacia Fine Chemicals of Piscataway, New Jersey. This material is a particulate dextran having a particle size range of 40–120 microns.

The anti-S protein factor-containing solution is passed through the two columns of "Sephadex" using 0.02 molar acetic acid as the eluant. The eluate is collected in two-milliliter fractions, numbering about 120 in all. Each of these fractions is assayed by the tryptophan uptake method for anti-S protein factor activity and is also analyzed for total polypeptide content by UV absorption, using a wavelength of 220 nanometers. Enough of the most active fractions (in terms of anti-S protein factor activity) are pooled together to provide a total polypeptide content in the range of about 60 micrograms to 1.5 milligrams. The resulting solution is then subjected to flash evaporation on a rotary evaporator to reduce its volume to about 1–3 ml.

The concentrated solution of anti-S protein factor plus impurities is then subjected to ion exchange chromatography using the following column:

Second Sulphonated Resin Column

The glass column is 200 centimeters high and has an internal diameter of 0.81 centimeter. The packing is the "Aminex 50-WX2" brand of cation exchange resin hereinbefore described. The packing is placed in the column and equilibrated with 0.2 normal sodium citrate buffer solution (pH 3.0) and the system is then brought to a temperature of 35° C.

The solution to be chromatographed is placed on the column and the column is then eluted using a 2 flask gradient elution system in which flask A contains 1 liter of 0.2 normal sodium citrate buffer solution (pH 3.0) and flask B contains 250 ml. of a buffer solution that has been prepared as follows: A solution is made of 14.6 grams citric acid, 20.6 grams sodium acetate, 3.1 ml. of glacial acetic acid and 800 ml. of distilled water; the pH of the resulting solution is adjusted to 4.0 by the addition of concentrated hydrochloric acid; and the volume of the solution is then brought to 1 liter by the addition of distilled water.

The eluate from the column is collected in 5 ml. fractions at a rate of about 4 to 5 fractions per hour. About 130 to 150 such fractions are collected in all. Each fraction is assayed for anti-S protein factor activity by the tryptophan uptake method. The fraction or fractions having the highest activity constitute solutions of anti-S protein factor that are relatively pure, i.e., are devoid of most of the other peptide material, cellular material, etc. that accompanied the factor when it was extracted from the beef hypothalamus in the tris citrate buffer solution. The fractions having the greatest concentration of anti-S protein factor are often found in the range of fraction numbers 80 to 86. Amino analysis of these fractions shows the factor to be a polypeptide constituting some combination of some of the following amino acids: glutamic acid, threonine, valine, leucine, phenylalanine, tyrosine, aspartic acid, serine, and glycine. Statistical evaluation of the amino acid analysis data, coupled with enzyme studies, indicates that the anti-S protein factor contains the tripeptide L-threonyl-L-valyl-L-leucine.

METHOD B

Alternatively, each pool from the foregoing described fractionation and assay by the tryptophan uptake method, may be treated separately and purified by reverse phase partition chromatography. The reverse phase partition chromatography is conducted using a Waters Associates Model 660 Solvent Programmer and a Waters Associates Model 6000 Solvent Delivery System in conjunction with a 6 or 10 foot by ⅜ inch Phenyl Porasil B Column obtainable from Waters Associates. The column is housed in a constant temperature compartment made of styrofoam blocks surrounding a Haake Type FE constant temperature bath. Introduction of samples to the column is effected by a Waters Associates Model U6K Universal Injector (1 microliter to 10 ml.), and the effluent from the column is collected with a Scientific Manufacturing Industries 1205 Fraction Collector. The effluent from column is monitored with a Beckman Model 25 Ultraviolet Spectrophotometer equipped with a Waters Associates LC-25 microcell assembly and with a Waters Associates R-401 Differential Refractometer.

For each pool from the sulphonated resin column, the fraction is dried and then dissolved in 5–10 ml. of solvent and injected on the column. The elution from the column is monitored for refractive index as well as absorbance at 225 nanometers. As peaks are eluted, the flow from the column is stopped and a sample is scanned for UV absorbance from 350 to 210 nanometers. Fractions of 5 milliliters each are collected and homogeneous peaks are pooled. The fraction, or pools, are taken to dryness and submitted for amino acid analysis and for tryptophan uptake analysis to determine the peaks having inhibition activity.

The fraction containing the L-threonyl-L-valyl-L-leucine may be N-acylated and/or esterified in accordance by substantially the same procedures set forth in Examples 10, 15 and 16.

As indicated above, research concerning schizophrenia has led to the isolation of an α-2-globulin (alpha-helical S-protein) from plasma of schizophrenic patients which has activities different from similar α-2-globulin (random S-protein) obtained from plasma of normal individuals. See Frohman, et al., *Recent Advances in Biological Psychiatry*, supra. The alpha-helical S-protein isolated from schizophrenic patients, when, for instance, administered to rats provides observable psychological responses in the rats. Caldwell, et al., in *Biological Psychiatry*, supra, indicate that administration of the alpha-helical S-protein to rats reduces self-stimulation for pleasure of the rats. Employing the procedures established by Caldwell, et al., various peptides of this invention are evaluated to determine their ability to reverse the effect of alpha-helical S-protein. In this manner the activity of components of this invention for alleviating the symptoms of schizophrenia in humans is illustrated. It has also been found that peptides which counteract the activity of the alpha-helical S-protein exhibit tryptophan uptake inhibition, and, as noted in Example 17, the tryptophan uptake analysis can be employed to assist in isolating peptide fractions which are active against the alpha-helical S-protein.

EXAMPLE 18

The procedure for intracranial self-stimulation in rats described at pages 237 to 239 of Caldwell, et al., *Biological Psychiatry*, supra (herein incorporated by reference in its entirety), is essentially repeated except as indicated below. The rats having the electrodes for stimulation planted in the median forebrain bundle are tested to determine the number of bar presses to be expected from the animals in a given period of time. The alpha-helical S-protein is intercisternally administered, and the number of bar presses is observed to drop to about 77 percent of the previous amount. Various polypeptides are intramuscularly administered to the rats in an amount of 0.2 mg/kg of body weight to determine whether the polypeptides reverse the effect of the alpha-helical S-protein. Tryptophan uptake are also conducted for the tested polypeptides. The tryptophan uptake inhibition is determined at 10 minutes. The results of the tests are provided in the following table.

| Peptide Administered | Tryptohan Uptake Inhibition % | Bar Presses Restoration % |
|---|---|---|
| Threonylvalylleucine | 19.8 | 85 |
| N-Acetyl-threonylvalylleucine | 20.2 | 100 |
| Glycylthreonylvalylleucine | 24.3 | 100 |
| Phenylalanylprolylthreonyl-vallylleucylprolyl phenylalanine | 39.5 | 100 |
| N-Acetyl-threonylvalylleucinamide | 56.5 | 100 |
| Threonylvalylleucinamide | 21.6 | 90 |
| Threonylvalylisoleucine | 5.6 | 41 |

The following polypeptides are tested for tryptophan uptake inhibition. The tryptophan uptake inhibition is determined at 10 minutes.

| Peptide Administered | Tryptophan Uptake Inhibition % |
|---|---|
| N-α-Acetyl-Threonylvalyleucine, methyl ester | 24.2 |
| N-α-Acetyl-tyrosylthreonyl-valylleucine | 21.3 |
| Prolylthreonylvalylleucyl-prolylgylcine | 44.2 |

The following polypeptides are tested for tryptophan uptake inhibition at times of 10, 15 and 30 minutes.

| Peptide Administered | Tryptophan Uptake Inhibition % | | |
|---|---|---|---|
| | Time: 10 min. | 15 min. | 30 min. |
| D-Alanyl-L-threonyl-L-valyl-L-leucine | 15 | 16 | 0 |
| L-Threonyl-L-valyl-D-leucine | 12 | 18 | 21 |

The foregoing data illustrate the use of D configuration-containing aminoacid moieties to inhibit tryptophan uptake. As demonstrated with D-alanyl-L-threonyl-L-valyl-L-leucine, after a period of time the inhibition of tryptophan uptake may be diminished. However, the essential polypeptide having the T-V-L structure exhibited an enhanced duration of activity when the leucine moiety was in the D configuration.

The following polypeptides are similarly tested but for comparison purposes. The tryptophan uptake inhibition is determined at 10 minutes.

| Peptide Administered | Tryptophan Uptake Inhibition % | Bar Presses Restoration % |
|---|---|---|
| Glycylglycylglycine | 0 | 3 |
| O-Benzyl-threonylvalylleucinamide | 0 | toxic |
| N-α-Acetyl-O-benzyl-threonyl-valylleucinamide | 0 | toxic |
| Benzyl-O-benzyl-threonylvalyl-leucate hydrochloride | 0 | toxic |
| L-Threonyl-L-valyl-L-leucyl-D-alanine | 2 | not tested |

As illustrated in the foregoing data relating to the testing of L-threonyl-L-valyl-L-leucyl-D-alanine, the presence on the (L) moiety of the essential T-V-L structure of a substituent which is relatively difficult to hydrolyze from a carboxylic function of an aminoacid, renders the peptide without significant tryptophan uptake activity.

Following essentially the same procedures as described above, N-acetyl-tyrosylthreonylvalylleucine, prolylthreonylvalylleucylprolylglycine are tested to determine their effect on rats which have been administered the alpha-helical S-protein. It is found that each of these polypeptide-containing materials restores the bar pressing activity of the rats. Other polypeptides exhibiting activity useful for alleviating the symptoms of schizophrenia include threonylvalylleucylarginine.

It is claimed:
1. A compound of formula

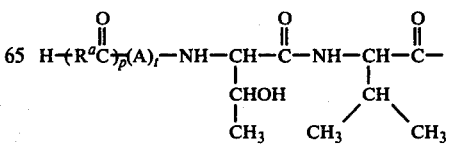

-continued

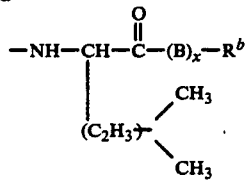

wherein A is an α-monoiminoacyl radical containing 2 to about 10 carbon atoms; B is a hydrolyzable α-monoiminoacyl radical containing 2 to about 10 carbon atoms; $R^a$ is alkylene of 1 to about 20 carbon atoms; $R^b$ is -$OR^e$ or -$NR^cR^d$, wherein $R^e$ is hydrogen or alkyl of 1 to about 20 carbon atoms, or aryl or aralkyl of 6 to about 24 carbon atoms, and $R^c$ and $R^d$ are the same or different and are hydrogen or lower alkyl; p is 0 or 1; t is 0 to 5; x is 0 to 5, wherein the sum of t and x is 0 to 5; and pharmaceutically-acceptable salts thereof.

2. The compound of claim 1 wherein the

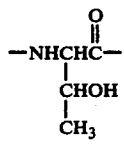

moiety is threonyl, and B, if optically active, is in the L-configuration.

3. The compound of claim 2 wherein the

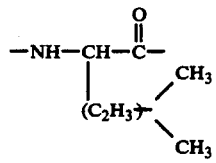

moiety is leucyl.

4. The compound of claim 3 wherein A and B are the same or different peptide moieties selected from the group consisting of prolyl, threonyl, allothreonyl, leucyl, isoleucyl, glycyl, seryl, arginyl, phenylalanyl, glutamyl, aspartyl, and alanyl.

5. The compound of claim 3 wherein

is acetyl.

6. The compound of claim 3 wherein $R^b$ is methoxy.
7. The compound of claim 3 wherein $R^b$ is -$NH_2$.
8. The compound of claim 3 wherein $R^b$ is -OH.
9. The compound of claim 3 wherein the

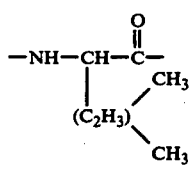

moiety is D-leucyl.

10. The compound of claim 1 which is L-threonyl-L-valyl-D-leucine.

11. The compound of claim 1 which is N-acetyl-L-threonyl-L-valyl-L-leucine.

12. The compound of claim 1 which is N-acetyl-threonylvalylleucinamide.

13. The compound of claim 3 wherein the

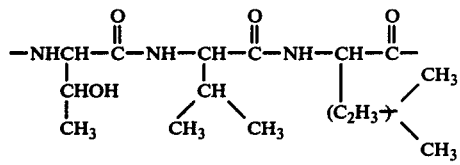

moieties are L-threonyl-L-valyl-L-leucyl.

14. The compound of claim 1 which is L-threonyl-L-valyl-L-leucine.

15. A pharmaceutical composition comprising a pharmaceutically-acceptable carrier and an effective amount of a compound of the formula

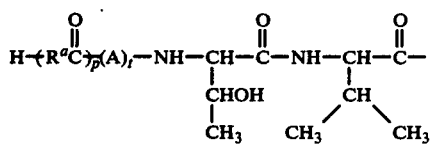

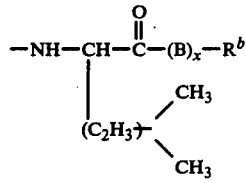

wherein A is an α-monoiminoacyl radical containing 2 to about 10 carbon atoms; B is a hydrolyzable α-monoiminoacyl radical containing 2 to about 10 carbon atoms; $R^a$ is alkylene of 1 to about 20 carbon atoms; $R^b$ is -$OR^e$ or -$NR^cR^d$ wherein $R^e$ is hydrogen or alkyl of 1 to about 20 carbon atoms, or aryl or aralkyl of 6 to about 24 carbon atoms, and $R^c$ and $R^d$ are the same or different and are hydrogen or lower alkyl; p is 0 or 1; t is 0 to 5; x is 0 to 5 wherein the sum of t and x is 0 to 5; and pharmaceutically-acceptable salts thereof.

16. The composition of claim 15 wherein the

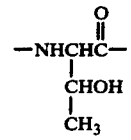

moiety is threonyl, and B, if optically active, is in the L-configuration.

17. The composition of claim 16 wherein the

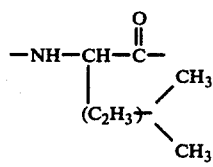

moiety is leucyl.

18. The composition of claim 17 wherein A and B are the same or different peptide moieties selected from the group consisting of prolyl, threonyl, allothreonyl, leucyl, isoleucyl, glycyl, seryl, arginyl, phenylalanyl, glutamyl, aspartyl, and alanyl.

19. The composition of claim 17 wherein

is acetyl.

20. The composition of claim 17 wherein $R^b$ is methoxy.
21. The composition of claim 17 wherein $R^b$ is -NH$_2$.
22. The composition of claim 17 wherein $R^b$ is -OH.
23. The composition of claim 17 wherein

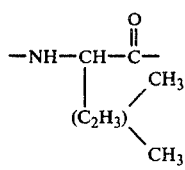

moiety is D-leucyl.

24. The composition of claim 15 wherein said compound is L-threonyl-L-valyl-D-leucine.
25. The composition of claim 15 wherein said compound is N-acetyl-L-threonyl-L-valyl-L-leucine.
26. The composition of claim 15 wherein said compound is N-acetylthreonylvalylleucinamide.
27. The composition of claim 15 wherein the

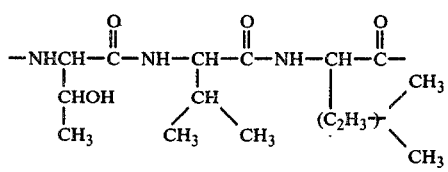

moieties are L-threonyl-L-valyl-L-leucyl.

28. The composition of claim 15 wherein said compound is L-threonyl-L-valyl-L-leucine.
29. A compound of the formula

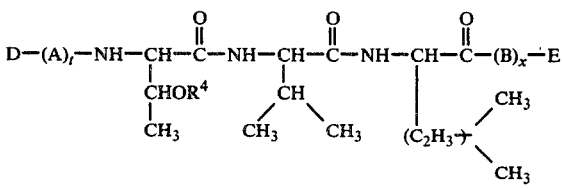

IV.

wherein A is an α-monoiminoacyl radical containing 2 to about 10 carbon atoms; B is a hydrolyzable α-monoiminoacyl radical containing 2 to about 10 carbon atoms; D is -H or an α-amino-protecting group; E is -OH, a terminal carboxylic-protecting group, a metal hydroxide complex or an acid addition salt; $R^4$ is H, alkyl of 1 to 20 carbon atoms, acyl of 1 to about 20 carbon atoms, tetrahydropyranyl, or monovalent metal, t is 0 to 5; x is 0 to 5, wherein the sum of t and x is 0 to 5; and pharmaceutically-acceptable salts thereof.

30. The compound of claim 29 wherein the

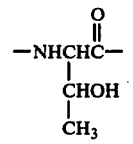

moiety is threonyl, and B, if optionally active, is in the L- configuration.

31. The compound of claim 29 wherein the

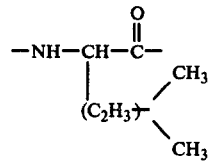

moiety is leucyl.

32. The compound of claim 29 wherein A and B are the same or different peptide moieties selected from the group consisting of prolyl, threonyl, O-benzylthreonyl, allothreonyl, leucyl, isoleucyl, glycyl, seryl, arginyl, phenylalanyl, glutamyl, aspartyl, and alanyl.

33. The compound of claim 31 wherein D is t-butyloxycarbonyl.
34. The compound of claim 31 wherein E is benzyloxy.
35. The compound of claim 31 wherein $R^4$ is benzyl.
36. The compound of claim 31 wherein the

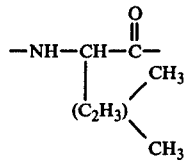

moiety is D-leucyl.

37. The compound of claim 30 wherein the

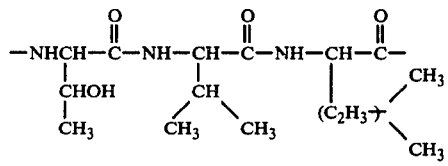

moieties are L-threonyl-L-valyl-L-leucyl.

* * * * *

UNITED STATES PATENT AND TRADEMARK OFFICE
CERTIFICATE OF CORRECTION

PATENT NO. : 4,146,614

DATED : March 27, 1979

INVENTOR(S) : Charles E. Frohman

It is certified that error appears in the above-identified patent and that said Letters Patent are hereby corrected as shown below:

Column 17, line 14, "t-glycylbutyloxycarbonyl-O-benzyl-threonyl" should be -- t-butyloxycarbonylglycyl-O-benzyl-threonyl --.

Column 25, line 48, "uptake" should be -- uptakes --.

Signed and Sealed this

Sixteenth Day of October 1979

[SEAL]

Attest:

RUTH C. MASON
Attesting Officer

LUTRELLE F. PARKER
Acting Commissioner of Patents and Trademarks